(12) United States Patent
Beyerlein

(10) Patent No.: US 7,641,634 B2
(45) Date of Patent: *Jan. 5, 2010

(54) CONTACT AND PENETRATION DEPTH SENSOR FOR A NEEDLE ASSEMBLY

(75) Inventor: Dagmar Bettina Beyerlein, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 11/773,377

(22) Filed: Jul. 3, 2007

(65) Prior Publication Data

US 2007/0255214 A1  Nov. 1, 2007

Related U.S. Application Data

(63) Continuation of application No. 10/029,608, filed on Dec. 20, 2001, now Pat. No. 7,247,149.

(51) Int. Cl.
*A61M 29/00* (2006.01)

(52) U.S. Cl. ..................................... 604/117

(58) Field of Classification Search ............... 604/116, 604/117, 21, 260, 272, 506
See application file for complete search history.

(56) References Cited

U.S. PATENT DOCUMENTS

| | | |
|---|---|---|
| 3,979,835 A | 9/1976 | Sumption et al. |
| 4,071,957 A | 2/1978 | Sumption et al. |
| 4,191,193 A | 3/1980 | Seo |
| 4,299,230 A | 11/1981 | Kubota |
| 4,535,773 A | 8/1985 | Yoon |
| 4,825,711 A | 5/1989 | Jensen et al. |
| 5,893,848 A | 4/1999 | Negus et al. |
| 6,024,703 A | 2/2000 | Zanelli et al. |
| 6,391,005 B1 | 5/2002 | Lum et al. |
| 6,569,144 B2 | 5/2003 | Altman |
| 6,692,466 B1 | 2/2004 | Chow et al. |
| 6,706,016 B2 | 3/2004 | Cory et al. |
| 7,247,149 B2 * | 7/2007 | Beyerlein ................ 604/117 |

* cited by examiner

*Primary Examiner*—Manuel A Mendez
(74) *Attorney, Agent, or Firm*—Blakely, Sokoloff, Taylor & Zafman LLP

(57) ABSTRACT

An apparatus is disclosed. The apparatus includes a needle to contact and penetrate tissue. The apparatus also includes a device coupled to the needle, wherein the device detects the needle contacting the tissue, and measures depth of tissue penetration.

16 Claims, 11 Drawing Sheets

CONTACT AND PENETRATION DEPTH SENSOR FOR A NEEDLE ASSEMBLY

This application is a continuation of U.S. patent application Ser. No. 10/029,608, filed on Dec. 20, 2001 now U.S Pat. No. 7,247,149.

BACKGROUND

The present invention relates to a needle assembly. More particularly, the invention relates to contact and penetration depth sensor for such a needle assembly.

There are many medical circumstances in which an increase in the supply of blood to living tissue is desirable. These include: burns and wound healing, in which the incorporation of angiogenic factors into artificial skin may facilitate the formation of blood vessels in the healing wound and reduce the risk of infection; cardiovascular disease, in which repair of anginal or ischemic cardiac tissue may be enhanced by causing the ingrowth of new blood vessels; stroke, where increased blood supply to the brain may reduce the risk of transient ischemic attack and/or cerebral arterial deficiency; and peripheral vascular disease, in which blood flow in the extremities is increased through the formation of new vessels. In each case, the growth of new blood vessels may increase the volume of blood circulating through the tissue in question, and correspondingly may increase the amount of oxygen and nutrients available to that tissue. However, some individuals are unable to generate sufficient collateral vessels to adequately increase the volume of blood through the tissue.

SUMMARY

The present invention, in one aspect, describes an apparatus which includes a needle and a device. The needle contacts and penetrates tissue. The device is coupled to the needle, where it detects the needle contacting the tissue, and measures the depth of tissue penetration.

In another aspect, the present invention describes a method. The method includes providing a needle tip, coupling a first conductive element to the tip, and providing a second conductive element at a predetermined distance away from the first conductive element. A spring-loaded assembly separates the first conductive element from the second conductive element. When the needle tip penetrates tissue, the tissue eventually comes into to contact with the first conductive element. As the needle continues through the tissue, the spring assembly compresses and allows the first conductive element to come into contact with the second conductive element. The contact between the two elements completes an electrical circuit and provides feedback to the user indicating that the needle has penetrated the tissue to a desired depth.

DETAILED DESCRIPTION

In recognition of the above-stated challenges associated with generation of sufficient collateral vessels, embodiments for providing a method and apparatus for delivering treatment agents to help stimulate the natural process of therapeutic angiogenesis is described. In particular, the embodiments include a needle sensor assembly to provide contact and penetration depth sensing for localized, periadvential delivery of a treatment agent(s) to promote therapeutic angiogenesis. However, the embodiments may be useful in other related applications for intravascular delivery of therapeutic agents. Consequently, for purposes of illustration and not for purposes of limitation, the exemplary embodiments are described in a manner consistent with such use, though clearly the invention is not so limited.

In connection with the description of the various embodiments, the following definitions are utilized:

"Therapeutic angiogenesis" refers to the processes of causing or inducing angiogenesis.

"AngiogenesisI" is the promotion or causation of the formation of new blood vessels in the ischemic region.

"Ischemia" is a condition where oxygen demand of the tissue is not met due to localized reduction in blood flow caused by narrowing or occlusion of one or more vessels.

"Occlusion" is the total or partial obstruction of blood flow through a vessel.

"Treatment agent" includes pharmacological and genetic agents directed to specific cellular binding sites (e.g., receptor binding treatment agents).

Figure 1:
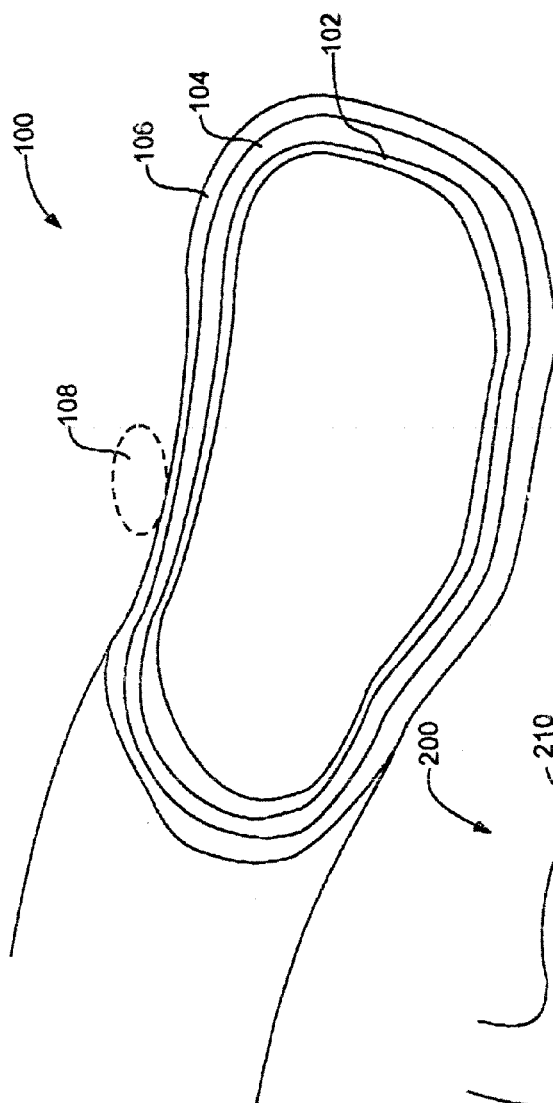
FIG. 1 illustrates a non-diseased artery.

Referring to FIG. 1, a non-diseased artery is illustrated. Artery 100 includes an arterial wall having a number of layers. An innermost layer 102 is generally referred to as the intimal layer that includes the endothelium, the subendothelial layer, and the internal elastic lamina. The media layer 104 is the middle layer and is bounded by external elastic laminae. An adventitial layer 106 is the outermost layer. Beyond the adventitial layer 106 lies the extravascular tissue including an area 108 referred to as a periadvential site or area.

Figure 2:
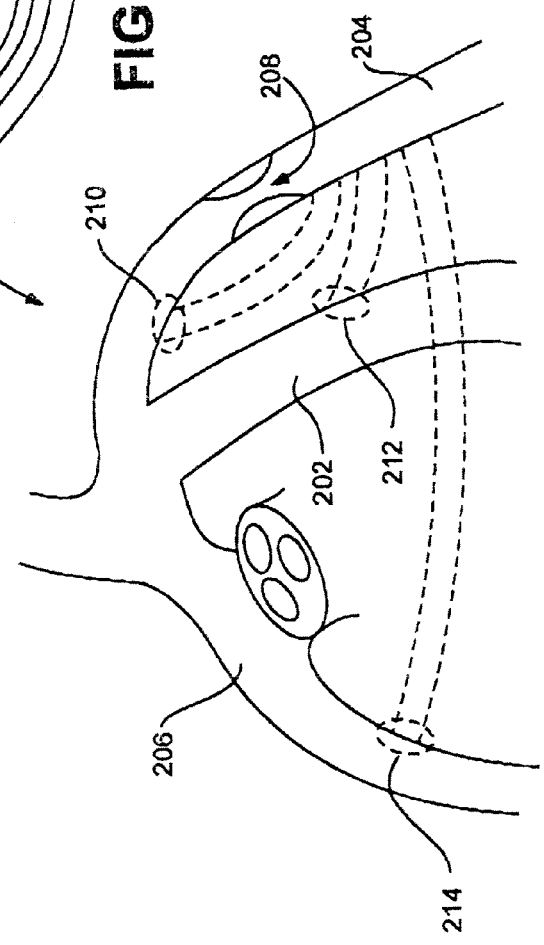
FIG. 2 illustrates components of a coronary artery network.

FIG. 2 illustrates components of a coronary artery network. In this simplified example, vasculature 200 includes Left anterior descending artery (LAD) 202, left circumflex artery (LCX) 204 and right coronary artery (RCA) 206. Occlusion 208 is shown in LCX 204. Occlusion 208 limits the amount of oxygenated blood flow through the LCX 204 to the myocardium, resulting in ischemia of this tissue.

To improve the function of the artery network, it is generally desired to remove or reduce the occlusion 208 (e.g., through angioplasty or atherectomy), bypass the occlusion 208 or induce therapeutic angiogenesis to makeup for the constriction and provide blood flow to the ischemic region (e.g., downstream of the occlusion 208). The illustrated figure shows therapeutic angiogenesis induced at site 210 (associated with LCX 204). By inducing therapeutic angiogenesis at site 210, permanent revascularization of the network is accomplished, thus compensating for reduced flow through LCX 204. The following paragraphs describe techniques and an apparatus suitable for inducing therapeutic angiogenesis.

One concern of introducing sustained-release treatment agent compositions into or adjacent to blood vessels or the myocardium is that the composition is accurately located and remains (at least partially) at the treatment site for the desired treatment duration (e.g., two to eight weeks). Accordingly, in one embodiment, an apparatus (a catheter assembly) is described for accurately delivering a treatment agent to a location in a blood vessel (preferably beyond the media layer 104) or in the periadvential space 108 adjacent to a blood vessel, or to another tissue location such as the tissue of the myocardium. It is appreciated that a catheter assembly is one technique for introducing treatment agents and the following description is not intended to limit the application or placement of the treatment agent.

In general, the delivery apparatus provides a system for delivering a substance, such as a treatment agent or a combination of treatment agents optionally presented as a sustained release composition, to or through a desired area of a blood vessel (a physiological lumen) or tissue in order to treat a localized area of the blood vessel or to treat a localized area of tissue possibly located adjacent to the blood vessel. The delivery apparatus includes a catheter assembly, which is intended to broadly include any medical device designed for insertion into a blood vessel or physiological lumen to permit injection and/or withdrawal of fluids or for any other purpose.

Figure 3:
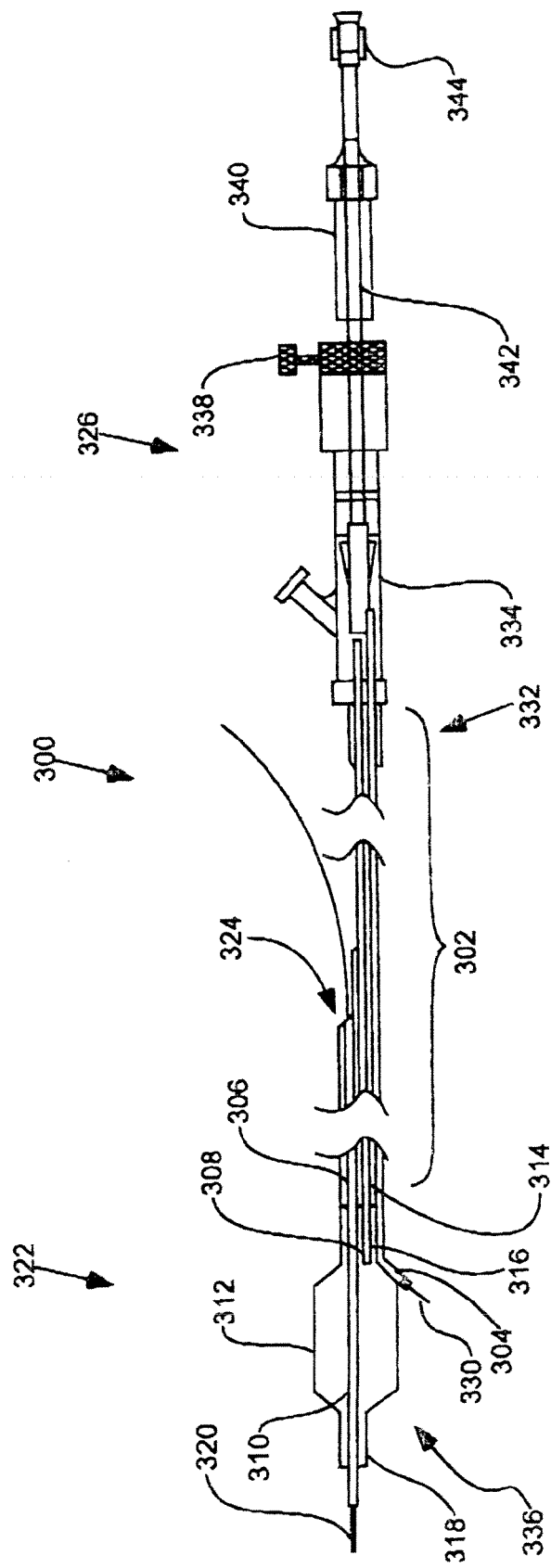
FIG. 3 shows cross-sectional view of a catheter-based needle drug delivery device.
Figure 4:
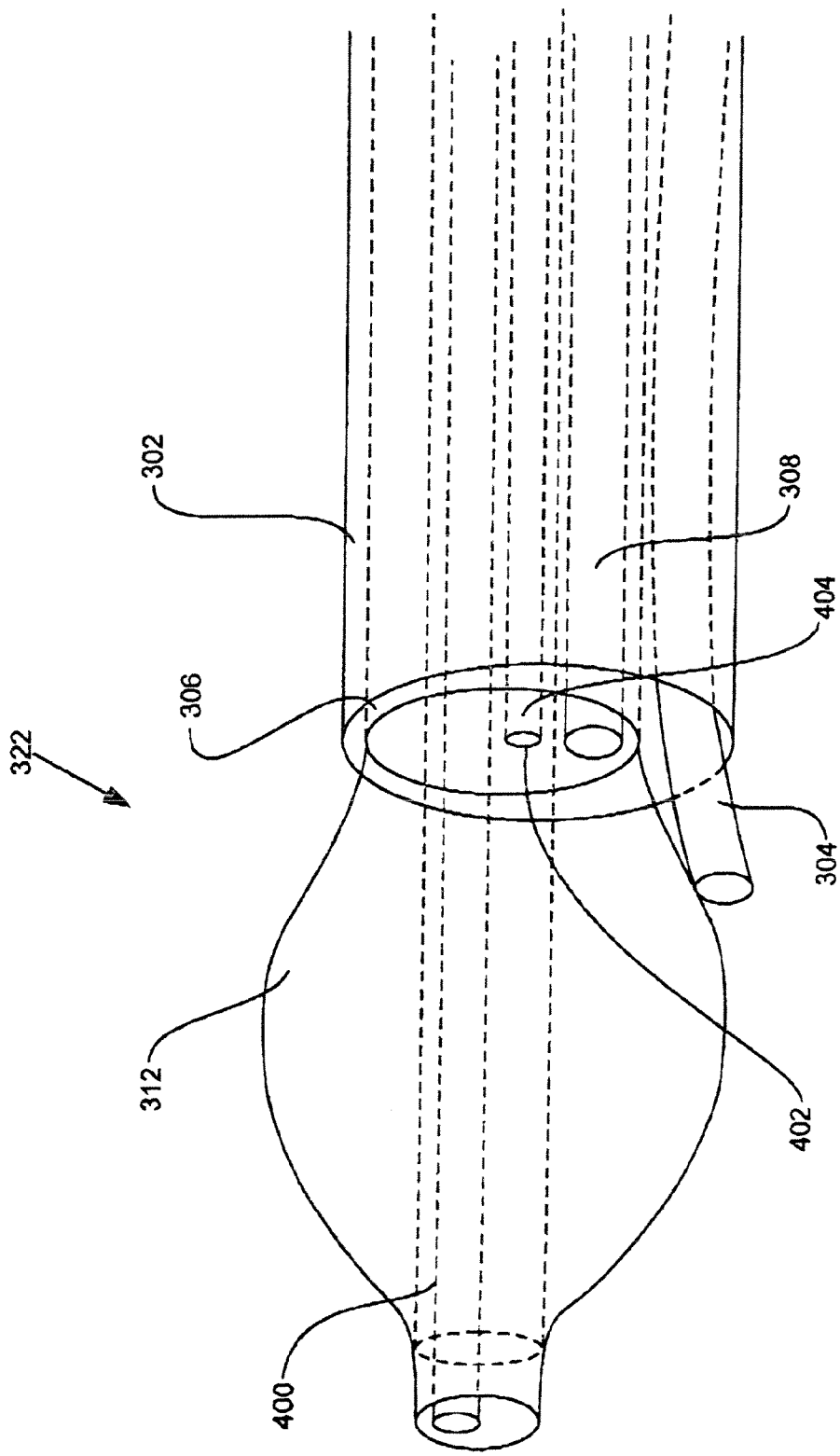
FIG. 4 illustrates the distal end of the drug delivery device in detail.

FIGS. 3 and 4 show cross-sectional views of the catheter-based needle drug delivery device 300. In particular, FIG. 4 illustrates the distal end 322 of the drug delivery device 300 in detail. This device is similar in certain respects to the delivery apparatus described in commonly-owned, U.S. patent application Ser. No. 09/746,498 (filed Dec. 21, 2000) titled "Directional Needle Injection Drug Delivery Device", of Chow et al., and incorporated herein by reference.

In general, the device 300 includes an elongated body 302 that surrounds a needle lumen 304 and an inner lumen 306. Housed within the inner lumen 306 are a fluid lumen 308 and an inner member 310 that also includes a guide wire lumen 400 and ultrasonic element lumen 402. An inflatable balloon 312 is attached to a distal end 314 of the inner lumen 306 and the inner member 310. In general, the proximal end 316 of the balloon 312 is attached to a distal end 314 of the inner member 310.

Extending partially along the length of the device 300 is the inner member 310. As shown in FIGS. 3 and 4, a portion of the inner member 310 protrudes out of the distal end 318 of the balloon 312. Housed within and along the length of the inner member 310 are two lumens. The first lumen 400, i.e. the guide wire lumen, provides a passageway for a movable guide wire 320. The guide wire 320 extends from beyond the distal end 322 of the device 300 to a guide wire exit 324 located near the proximal end 326 of the device 300. The guide wire 320 serves as the steering mechanism and lumens of the patient to the chosen target site. Overall length and diameter of the guide wire 320 are within the range of approximately 74.8 inch to 118.1 inch and 0.0152 inch to 0.019 inch, respectively. The guide wire 320 may be fabricated from a variety of materials including, but not limited to, stainless steel, platinum and polymers. These and other similar materials exhibit the required structural properties, such as strength and flexibility, desired in guide wire elements 320. The second lumen 402, i.e. the ultrasonic element lumen, of the inner member 310 houses the detractable ultrasonic element 404.

The device 300 also includes a retractable needle 330 housed in the needle lumen 304 and freely movable therein. The hollow, tubular shaped need 330, having an inner diameter within the range of approximately 0.002 inch to 0.010 inch and an outer diameter within the range of approximately 0.004 inch to 0.012 inch provides a fluid conduit that extends from the proximal end 332 to the distal end 334 of the needle 330. The distal end 334 of the needle 330 terminates in a curved, tissue-piercing tip having an angle of curvature between 30 degrees to 90 degrees. Needle curvature facilitates placement of the needle tip near to or within the desired target tissue. Further, to allow easy needle deployment from and retractability into the lumen, yet provide sufficient structural strength for insertion into tissue, the needle 330 is preferably fabricated from stainless steel NiTi (nickel titanium) or other similar semi-rigid materials. The needle may also be coated with fluoroscopically opaque materials to enhance its imaging capabilities on the fluoroscope.

Near the proximal end 332 of the needle 330, the needle 330 connects to an adapter 336 that attaches the needle 330 to a needle lock 338 and a needle adjustment puncture knob 340. The needle lock 338 is used to secure the needle 330 in place and prevent further movement of the needle 330 within the lumen once the needle 330 is located in the desired position. A needle adjustment knob 340 controls accurate needle extension out of the distal end of the catheter and depth of penetration into the tissue target. In general, the needle adjustment knob 340 is slidable along a proximal portion of the needle lumen or element 342 housing the needle 330. The element 342 includes various gradations or scalable markings along a portion of its length that correspond to the length of needle 330 extending out from the needle lumen 304. During use, the needle adjustment knob 340 that is also attached to the proximal end of the needle 330 is locked into position at a marking corresponding to the desired length of needle extension from the catheter. The knob 340 is then moved in a distal direction until it butts against the needle lock 338. Movement of the knob 340 also moves the needle 330, so that the predetermined length of needle 330 extends out from the needle lumen 304. The needle lock 338 is then used to secure the needle 330 in place and prevent further movement of the needle 330 within the lumen.

Located near the proximal end 326 of the device 300 is a drug injection port 344. The port 344 provides a connection for various dispensing elements such as a syringe, fluid pump, etc. In addition to drugs, other fluids including, but not limited to, therapeutic agents and diagnostic substances, may also be injected into the port 344 for delivery to the target site. Fluids injected into the port 344 travel through the needle 330 and are dispensed from the distal tip of the needle 330.

Figure 5A:
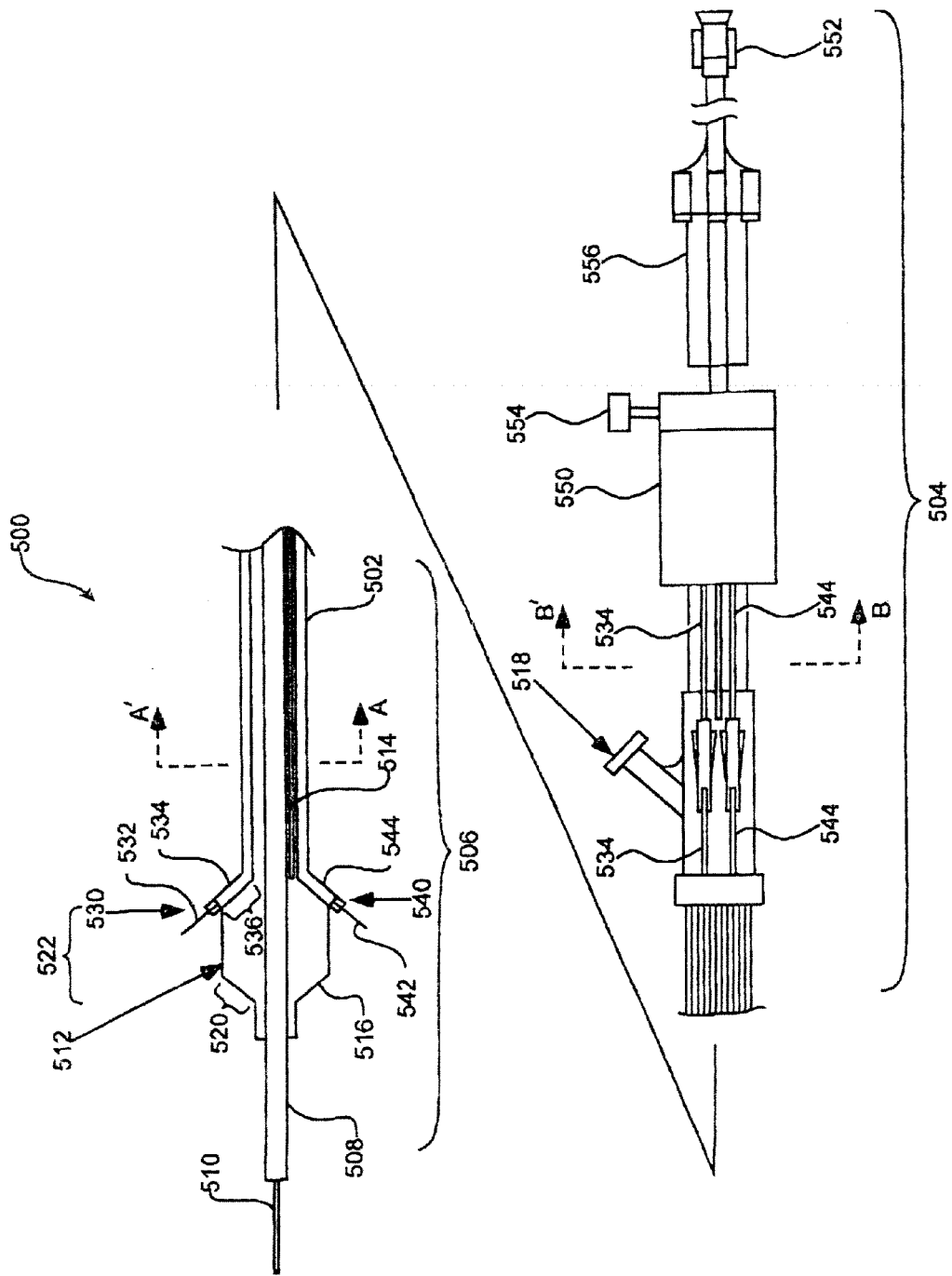
FIG. 5A illustrates cross-sectional view of another catheter-based drug delivery device.
Figure 5B:
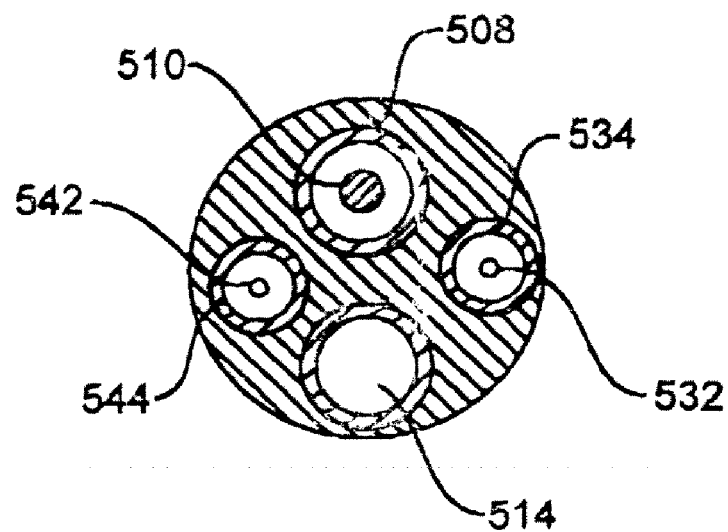
FIG. 5B shows a cross-sectional view of the catheter assembly through line A-A' of FIG. 5A at a distal end.
Figure 5C:
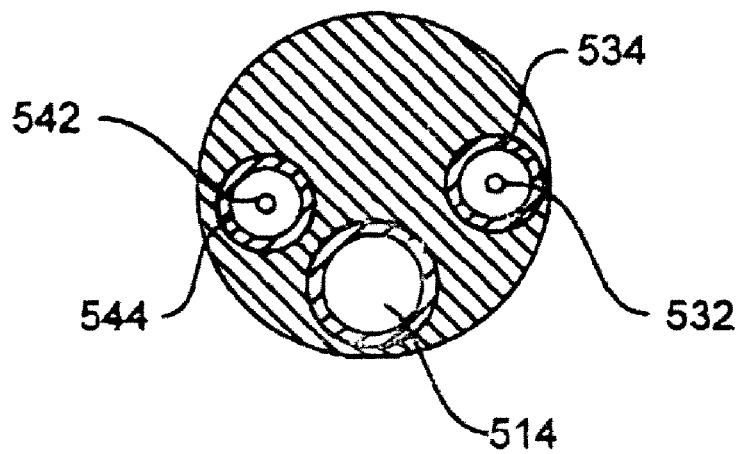
FIG. 5C shows another cross-sectional view of the catheter assembly through line B-B' of FIG. 5A at a proximal end.

Another delivery apparatus is illustrated in FIGS. 5A, 5B, and 5C. The apparatus includes a catheter assembly 500 which is defined by an elongated catheter body (cannula) 502 having a proximal end 504 and a distal end 506. FIG. 5B shows a cross-sectional view of the catheter assembly 500 through line A-A' of FIG. 5A (at a distal end 506). FIG. 5C shows another cross-sectional view of the catheter assembly 500 through line B-B' of FIG. 5A (at a proximal end 504).

Referring to FIGS. 5A and 5B, the catheter assembly 500 includes a catheter body 502 extending from the proximal end 504 to the distal end 506. In this example, a guidewire lumen 508 is formed within the catheter body 502 for allowing the catheter assembly 500 to be fed and maneuvered over the guidewire 510 (shown at this point within the guidewire lumen 508).

Balloon 512 is incorporated at the distal end 506 of the catheter assembly 500 and is inflated through a lumen 514 within the catheter body 502 of the catheter assembly 500. The balloon 512 includes a balloon wall or membrane 512 which is selectively inflatable to dilate from a collapsed configuration to a desired and controlled expanded configuration. The balloon 512 may be selectively dilated (inflated) by supplying a fluid into the inflation lumen 514 at a predetermined rate of pressure through an inflation port 518. The balloon 512 is selectively deflatable, after inflation, to return to the collapsed configuration or a deflated profile. In one embodiment, the balloon 512 may be defined by three sections, a distal taper 520, a medial working length 522, and a proximal taper 524. In one embodiment, the proximal taper 524 may taper at any suitable angle θ, typically between about 10° to less than about 90°, when the balloon 512 is in the expanded configuration.

The catheter assembly 500 shows two separate injection systems, 530 and 540, for the delivery of therapeutic agents. In one embodiment, the first delivery assembly 530 includes a needle 532 having a lumen with a diameter of, for example, 0.004 inch (0.010 cm) to 0.012 inch (0.030 cm). The needle 532 can be moved distally or proximally within a first needle sheath 534 formed in the catheter body 502.

A second delivery assembly 540 also includes a needle 542 that can be moved distally and proximally within a second needle sheath 544 formed in the catheter body 502. The needle sheaths 534 and 544 extend between the distal end 506 and the proximal end 504 of the catheter. Access to the proximal end of the delivery lumens 534 and 544 for insertion of needles 532 and 542, respectively, is provided through a hub 550.

Figure 6:
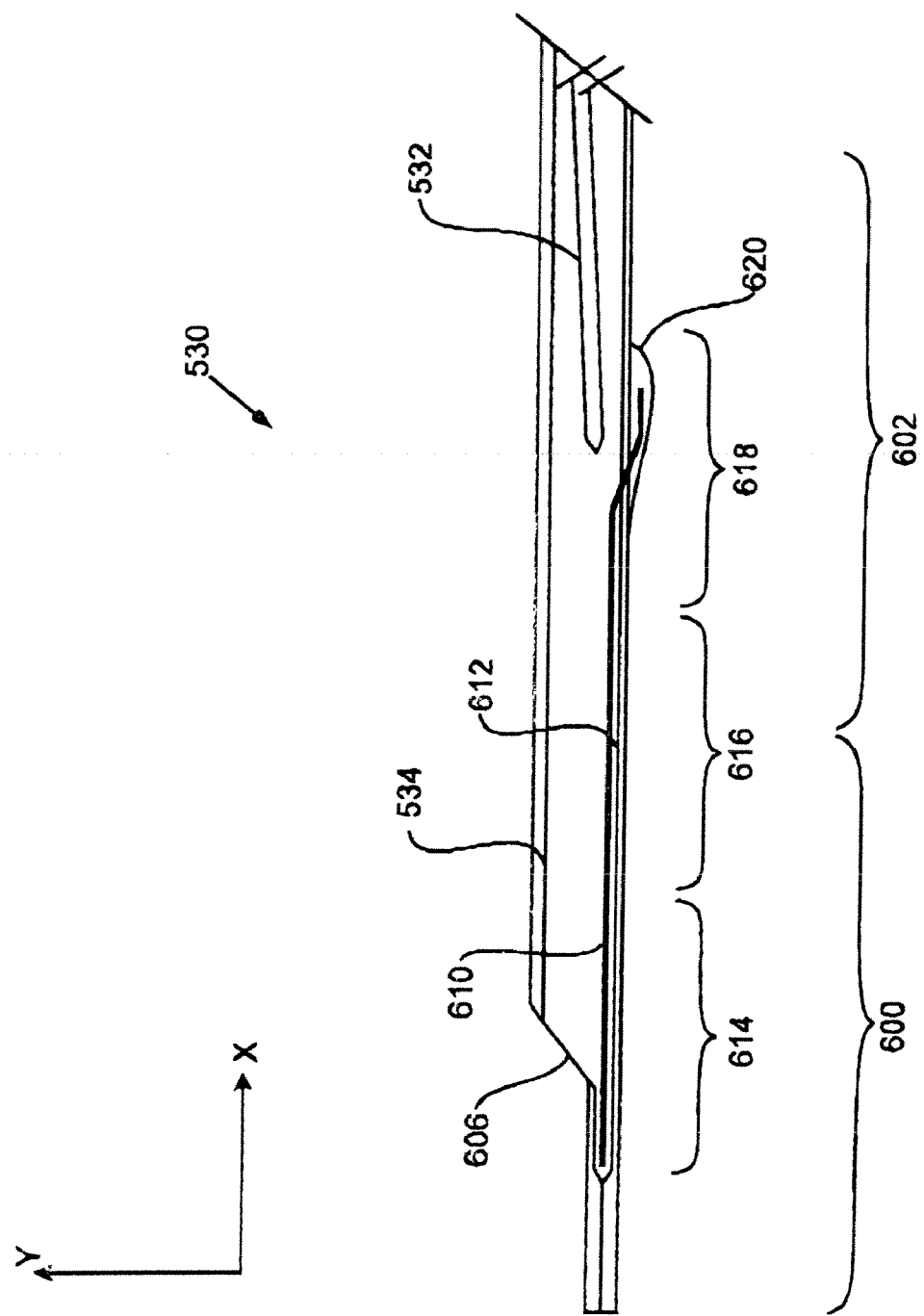
FIG. 6 illustrates a needle catheter assembly in a retracted position.
Figure 7:
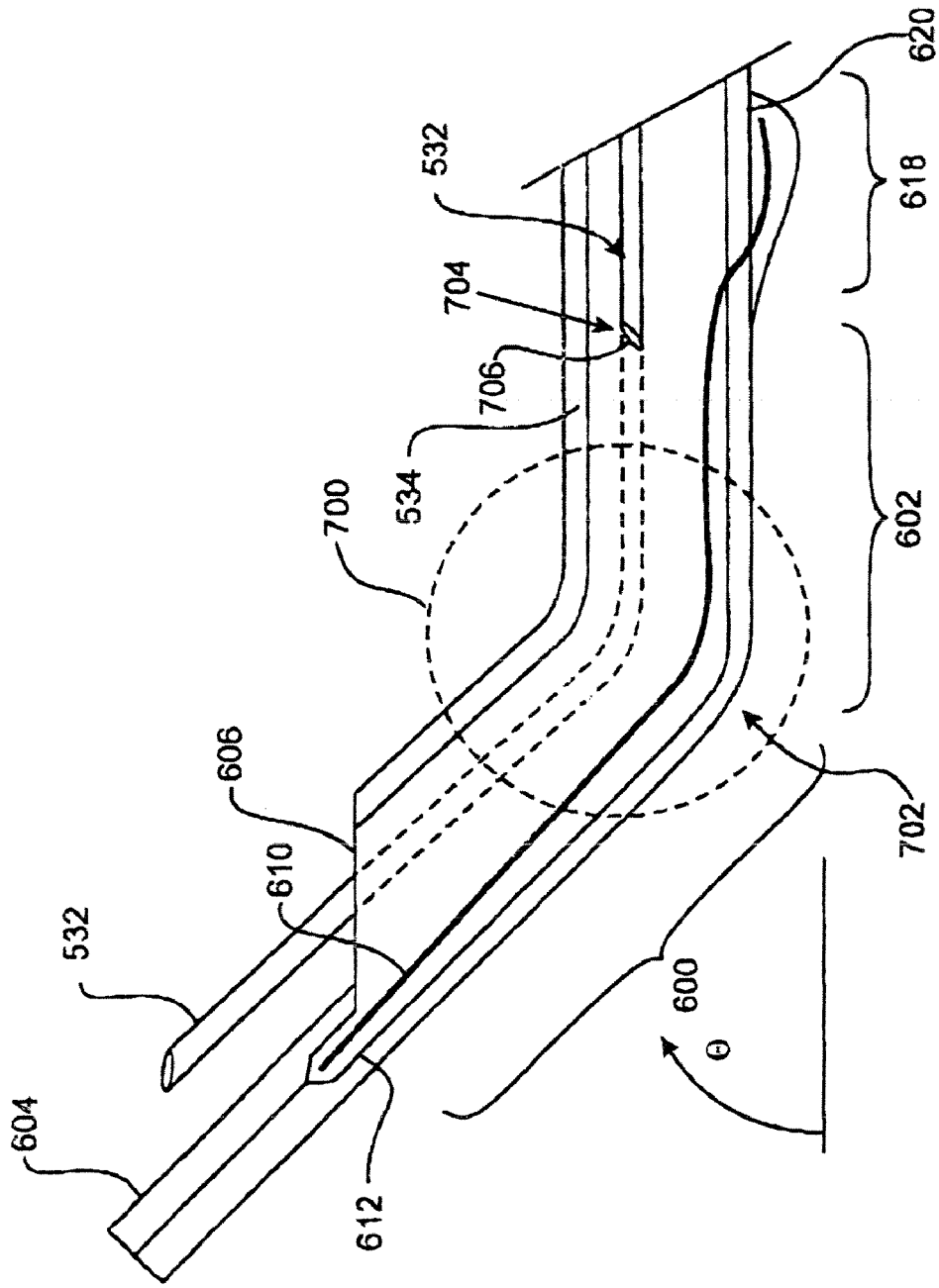
FIG. 7 illustrates the needle catheter assembly in an extended position.

FIGS. 6 and 7 show simplified sectional views of a therapeutic substance delivery assembly 530 in undeployed and deployed arrangements, respectively. The delivery lumen 534 includes a distal or first section 600 and a proximal or second section 602. The distal section 600 may include an extended section 604 that goes beyond opening 606 to provide a means for securing the needle sheath 534 to the balloon 512. For example, the extended section 604 may be adhered to the proximal balloon taper 524. In this manner, the needle sheath 534 is continually supported during, until, and after the needle 532 is extended from the delivery lumen 534.

In one embodiment, as shown in FIG. 7, the delivery lumen 534 includes a flexible region 700 that allows the distal section 600 of the needle sheath 534 to bend about a pivotal point 702 with respect to the proximal section 602. For example, to accomplish the pivotal movement, the distal section 600 of the needle sheath 534 is in contact with the proximal taper 524 of the balloon 512 (see FIG. 5A). Accordingly, in response to the inflation of the balloon 512, the distal section 600 moves relative to the proximal section 602 to form the bent region 700. In one embodiment, the distal section 600 may move from a substantially longitudinal position to a substantially perpendicular position. Thus, the angle θ of the bend region 700 may vary between 0° and 90°. In one example, after inflation of the balloon 512, angle θ may range from between about 10° and 90°, for example, 45°.

The needle 532 is moved distally within the needle sheath 534. Referring to FIG. 7, the needle 532 includes a tissue-piercing tip 704 having a dispensing lumen 706. In one embodiment, the lumen of the needle 532 may be pre-filled with a measured amount of a treatment agent. The lumen of the needle 532 connects the dispensing lumen 706 with a treatment agent injection port 552 (see FIG. 5A), which is configured to be coupled to various substance dispensing means of the sort known in the art, for example, a syringe or fluid pump. The injection port 552 allows a measured treatment agent to be dispensed from the dispensing lumen 706 as desired or on command.

The needle 532 is coupled at the proximal end 504 of the catheter assembly 500 in a needle lock 554 (see FIG. 5A). The needle lock 554 may be used to secure the needle 532 in position once the needle 532 has been either retracted and/or extended from the delivery lumen 534 as described below. In one embodiment, an adjustment knob 556 (see FIG. 5A) may be used to set the puncture distance of the needle 532 as it is extended out from the delivery lumen 534 and into the wall of the physiological lumen. The portion of the needle 532 protruding from the delivery lumen 534 may be of any predetermined length, the specific length being dependent upon the desired depth of calibrated penetration and the procedure for which delivery assembly 530 is to be used. The protruding length of the needle 532 may be from about 250 microns to about four centimeters (cm). It is appreciated that other mechanisms for securing the needle 532 at a retracted or extended position may alternatively be used, including the incorporation of a mechanical stop optionally including a signaling (e.g., electrical signaling) device.

The needle 532 is slidably disposed in the delivery lumen 534, so that the needle 532 may move between a first retracted position (FIG. 6) and a second extended position (FIG. 7). In its first or retracted position, the tissue-piercing tip 704 is located inboard of the distal surface of the catheter body 502, so as to avoid damaging tissue during deployment of the catheter assembly 500. In its second or extended position, the tissue-piercing tip 704 is located outboard of the distal surface of the catheter body 302, so as to permit the needle tip 704 to penetrate the tissue surrounding the physiological passageway in which the catheter assembly 500 is disposed.

Referring again to FIGS. 6 and 7, a deflector 610 is disposed along an inner wall 612 of the delivery lumen 534. In one embodiment, the deflector 610 includes distal section 614, medial section 616 and proximal section 618. In one embodiment, the distal section 614 may be supported by the delivery lumen 534 by bonding the distal section 614 to the overhang section 604 of the delivery lumen 534. The medial section 616 of the deflector 610 may be disposed on the inner wall 612 of the delivery lumen 534, such that as the delivery lumen section 600 rotates relative to the delivery section 602 to form the bend region 700, the deflector 610 is positioned over the outside of the curvature of the bend region 700. The proximal section 618 exits out of the delivery lumen 534 and is adhered to an outside wall 620 of the delivery lumen 534 using an adhesive, such as glue or the like.

The deflector 610 may be any device that will provide a shield to protect the wall of the delivery lumen 534 while being small enough, such that the deflector 610 does not impact the track of the catheter assembly 500 in any significant manner. In one embodiment, the deflector 610 may be a ribbon member. The ribbon member may be made thin, flexible and resilient such that the ribbon member may move and bend as the delivery lumen sections 600, 602 bend and move relative to each other.

Figure 8:
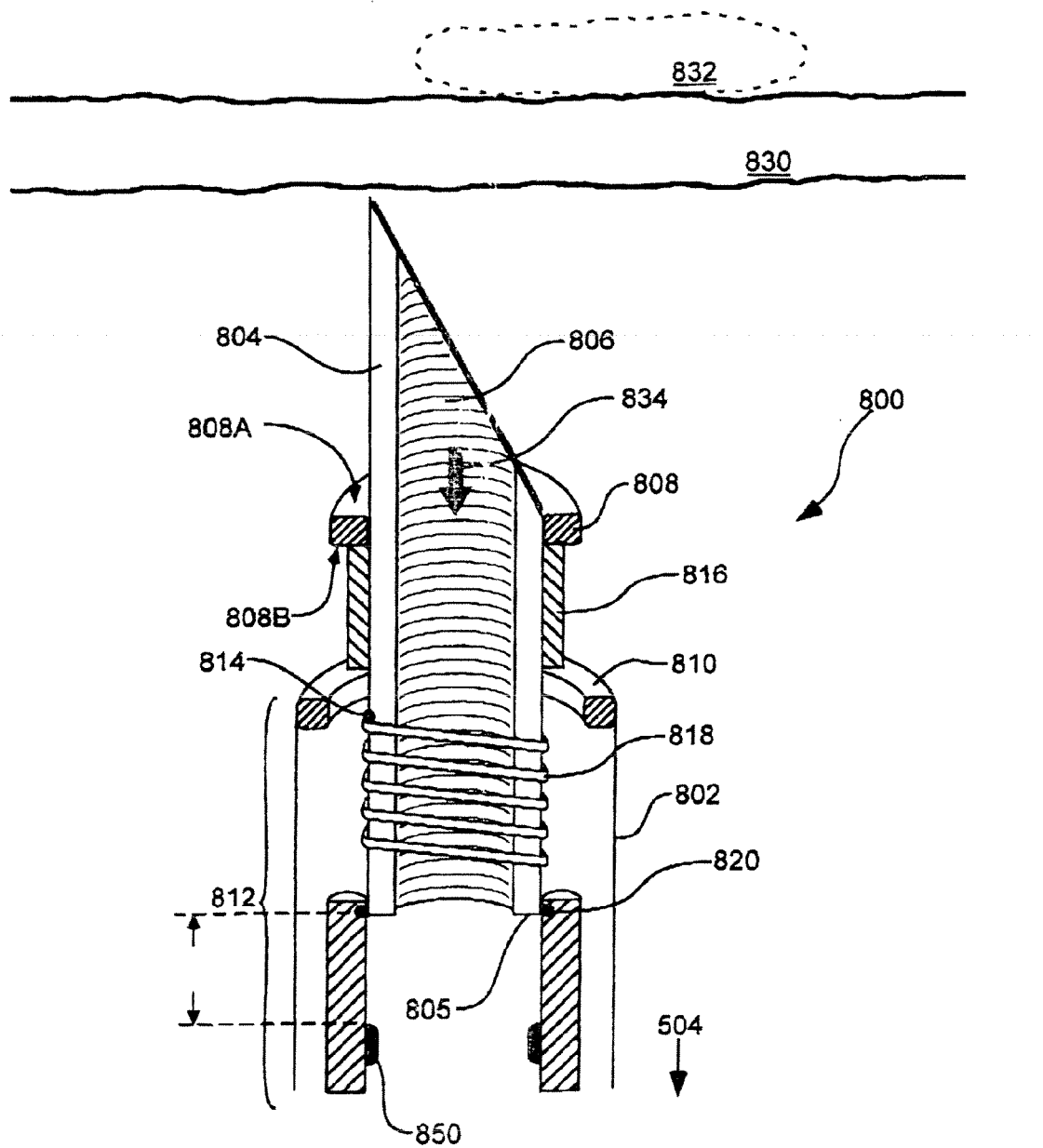
FIG. 8 illustrates a detailed cross-sectional view of an embodiment of a needle sensor assembly, prior to tissue engagement.
Figure 9:
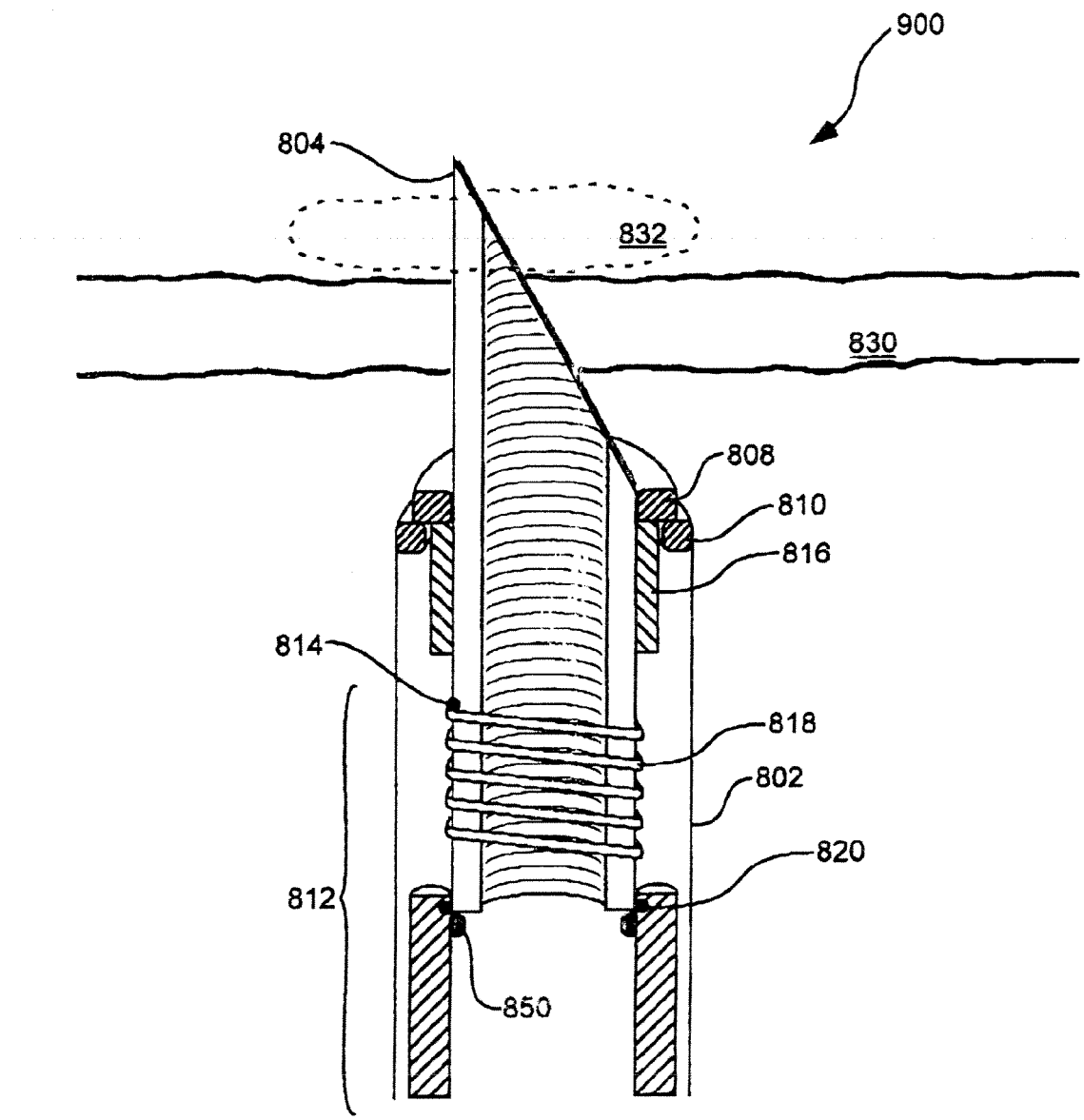
FIG. 9 illustrates a detailed cross-sectional view of the needle sensor assembly of FIG. 8, after tissue penetration.

A detailed cross-sectional view of an embodiment of a needle sensor assembly 800 disposed within a needle delivery lumen 802 is illustrated in FIG. 8. In some embodiments, needle sensor assembly may be a part of the drug delivery device 300 (see FIG. 3) described above. The needle sensor assembly enables, in one regard, detection of needle engagement and penetration depth of the tissue wall (i.e., tissue) 830 and/or the surrounding area 832. FIG. 8 illustrates the needle sensor assembly 800 prior to tissue engagement, while FIG. 9 illustrates the needle sensor assembly 900 after tissue penetration.

In the illustrated embodiment of FIG. 8, the needle sensor assembly 800 includes a needle sheath or delivery lumen 802, a needle 804, and a fluid dispensing port 806. Disposed around exterior distal portion of needle 804 is a conductive gasket or o-ring 808. Electrical contacts or contact ring 810, in this view, is disposed within delivery lumen 802 (as viewed concentrically around delivery lumen). Needle sensor assembly 800 also includes, in this embodiment, a spring assembly 812 disposed concentrically around needle 804 at a distance (as viewed) proximal to conductive gasket or o-ring 808, and a weld joint 814 between the spring assembly 812 and the needle 804. Needle sensor assembly 800 further includes an insulator 816 disposed around needle 804 between conductive gasket or o-ring 808 and spring assembly 812.

The engagement of the needle 804 to a tissue wall 830 may be detected by sensing the initial movement of the spring 818 in the spring assembly 812. As the needle tip 804 penetrates the tissue wall 830, resistance from the tissue wall 830 causes the spring 818 to compress. The needle continues to advance causing the spring 818 to compress further until a proximal surface 808A of the conductive gasket 808 comes into contact with the tissue wall 830, as shown in FIG. 9.

Substantially simultaneously, the proximal surface 808B of the conductive gasket 808 contacts the contact ring 810 in delivery lumen 802 to electrically indicate that the needle 804 has penetrated into the tissue wall 830 for a distance, which may be programmed (predetermined) by establishing the distance between the conductive gasket 808 and the contact ring 810. Once the needle 804 has been engaged and the penetration depth of the needle 804 has been determined, the needle sensor assembly 800 enables delivery of appropriate fluid to the tissue wall 830 and/or the surrounding area 832 through the fluid dispensing port 806.

Referring to FIG. 8, the conductive gasket 808 is attached to the needle 804. In one embodiment, the gasket 808 may be entirely conductive. In another embodiment, the distal surface 808A of the conductive gasket 808 includes a soft, rounded material (e.g., silicone or foam) so that injury to the tissue wall 830 may be minimized, while the proximal surface 808B includes conductive material to enable electrical signaling upon contacting the contact ring 810.

In some embodiments, the electrical contact or contact ring 810 may be formed as a ring and inserted through the needle sheath 802. In other embodiments, the electrical contact or contact ring 810 may be formed as contact terminal(s) attached to the needle sheath 802. Further, an insulator 816 (e.g., insulative material such as ceramic, polyimide, etc.) is deposited onto or otherwise attached (e.g., coupled via adhesive) to the needle shaft in an amount and over an area sufficient so that the electrical contact or contact ring 810 are isolated from the needle 804 (i.e., so that the shaft of needle 804 does not contact electrical contact or contact ring 810 over the travel distance of needle 804 within lumen 802.

Electrical connectivity from the contacts on the conductive gasket 808 and the contact ring 810 to a contact and penetration sensor on the proximal end 504 of the catheter assembly 500 may be made using several methods. In one method, insulated wires may be extended from the proximal end 504 of the catheter assembly 500 (see FIG. 5A) to each of the contacts 810. In another method, a wire/electrical conduit may be extruded into or sputtered onto the needle sheath 802. In a further method, a wire/electrical conduit may be inserted between two layers of the needle sheath 802. In an alternative method, the needle 804 may be used as one electrical conduit, while any one of the proposed methods may be used to create the conduit from the proximal end 504 to one or several contacts on the contact ring 810. The alternative method using the needle 804 may be feasible if the current required to operate the sensor is not excessive.

Figure 10:
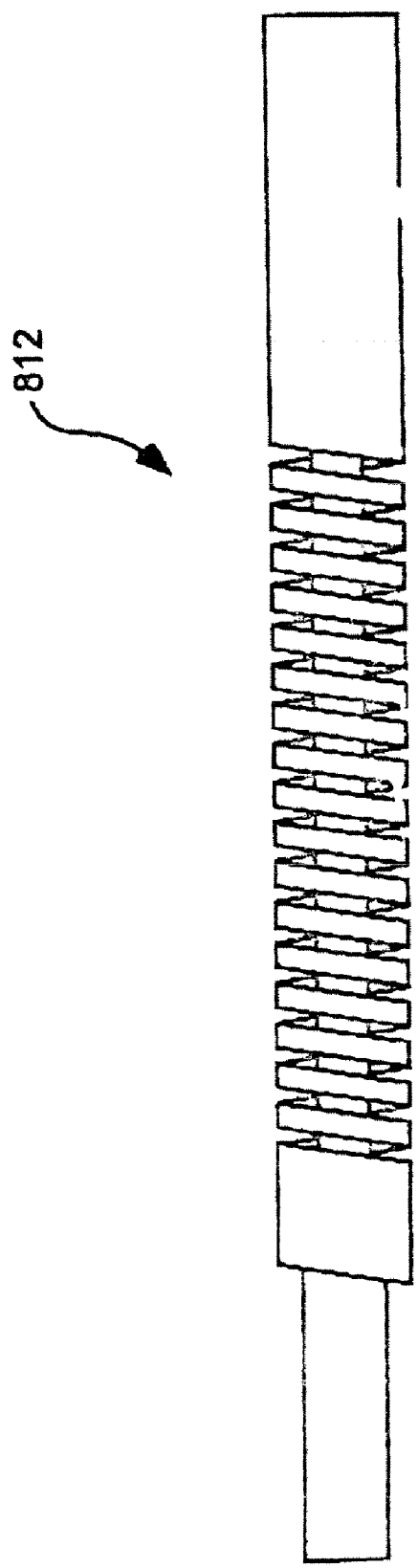
FIG. 10 illustrates a spring assembly machined from a tube.

The spring assembly 812, in one embodiment, may be machined from a hypotube as shown in FIG. 10. In another embodiment, the assembly 812 may be manufactured using a coil winding process. The spring has a deflection property selected to be sufficient to be actuated (deflect) in response to a resistive force F (see FIG. 9) by tissue wall 830 in response to penetration by needle 804. In responding to a resistive force from an arterial blood vessel, an appropriate deflection property for a spring is selected. The proximal end 805 of the needle 804 may slip fit into the spring assembly 812 at 820. Furthermore, the distal portion of the spring assembly 812 may be welded or otherwise attached to the needle 804 at the weld joint 814. In one embodiment, the proximal end of the spring is attached to the proximal portion of the needle (the tube with the larger inner diameter) using a weld joint as in 814. In another embodiment, the spring is machined out of the larger, proximal portion of the needle. Thus, the needle tip may detach from the assembly without appropriate attachment of the spring as described above. The device should also have a seal 850 on the inner diameter of the larger, proximal portion of the needle placed in a distance equivalent to the desired penetration depth from 805. This prevents fluid from leaking from the needle at the slip fit interface. (see FIGS. 8 and 9). In some embodiments, the distal sides of the seal 850 may be made conductive. Thus, in these embodiments, the seal 850 may be used to complete the circuit rather than the contact ring 810.

As the needle 804 is advanced from the proximal end 504 of the catheter assembly 500, the needle tip penetrates the tissue wall 830 and continues to advance until the conductive gasket 808 contacts the tissue wall 830. The resistance from the tissue wall 830 causes the spring 818 to compress. Moreover, the resistance forces the conductive gasket 808 and the attached needle 804 to move in the proximal direction 834, as shown. With continued tissue insertion pressure, the spring 818 continues to compress until the conductive gasket 808 comes into contact with the electrical contact(s) 810. This contact completes an electrical loop and triggers a signal (audible or visual) to the proximal end 504 of the catheter assembly 500 to indicate to an operator of the catheter assembly that the penetration of the needle 804 into the tissue wall 830 for a predetermined distance has been detected. The distance may be programmed by adjusting the distance between the conductive gasket 808 and the electrical contacts 810. In instances where the needle 804 is delivering a treatment agent to the periadvential area, the distance may be approximately 0.5 millimeter.

Figure 11:
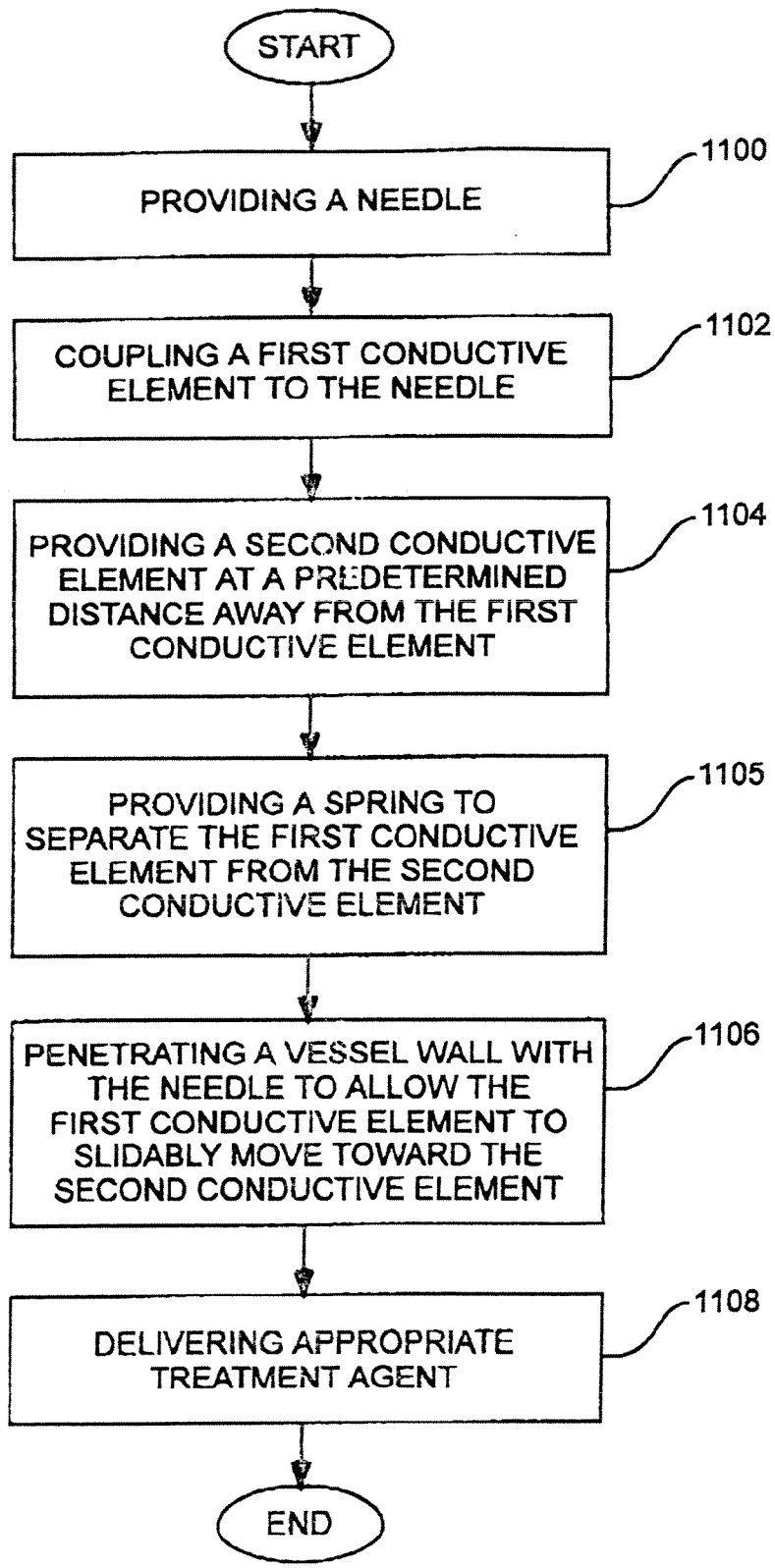
FIG. 11 is a flowchart illustrating a method for sensing tissue contact and penetration.

FIG. 11 is a flowchart illustrating a method for sensing tissue contact and penetration according to an embodiment of the present invention. The method includes providing a needle, at 1100. A first conductive element is coupled to the needle, at 1102. A second conductive element is then provided at a predetermined distance away from the first conductive element, at 1104. A spring may be used to separate the first conductive element from the second conductive element, at 1105. A tissue wall is penetrated with the needle to allow the first conductive element to slidably move toward the second conductive element, at 1106. When the conductive elements contact one another, a signal is provided to an operator that the fluid dispensing port of the needle is at the treatment site. Finally, appropriate treatment agent is delivered at 1108.

There has been disclosed herein embodiments for a needle sensor assembly to provide contact and penetration depth sensing for periadvential and local delivery of treatment agent to promote therapeutic angiogenesis. The needle penetration depth may be adjusted by appropriately configuring the conductive gasket 808 and the electrical contacts 810 within the needle sensor assembly 800.

While specific embodiments of the invention have been illustrated and described, such descriptions have been for purposes of illustration only and not by way of limitation. Accordingly, throughout this detailed description, for the purposes of explanation, numerous specific details were set forth in order to provide a thorough understanding of the present invention. It will be apparent, however, to one skilled in the art that the embodiments may be practiced without some of these specific details. For example, although the present embodiments describe the needle sensor assembly having conductive contacts, other non-conductive contacts may be used to determine the needle penetration depth. In other instances, well-known structures and functions were not described in elaborate detail in order to avoid obscuring the subject matter of the present invention. Accordingly, the scope and spirit of the invention should be judged in terms of the claims which follow.

What is claimed is:

1. An apparatus, comprising:
   an intravascular delivery device, comprising:
      a needle to contact and penetrate tissue; and
      a device coupled to the needle, the device comprising a conductive component which is movable relative to a first position, wherein the movement of the conductive component is in response to movement of the needle penetrating into tissue, the device being configured to indicate electronically when the conductive component is in the first position, wherein a movement of the needle corresponds to a depth of tissue penetration corresponding to a specific location within the tissue for delivery of a treatment agent.

2. The apparatus of claim 1, further comprising:
   a needle sheath disposed around a portion of the device and the needle to provide protection for the tissue from the needle.

3. The apparatus of claim 1, wherein the needle includes a tube to enable delivery of fluid through the needle.

4. The apparatus of claim 1, wherein a portion of the needle is insulated.

5. The apparatus of claim 1, further comprising:
   a spring assembly coupled to the needle and to the conductive component.

6. The apparatus of claim 5, wherein the spring assembly includes a spring which compresses in response to an engagement of the needle to the tissue.

7. The apparatus of claim 5, further comprising:
   a slip fit joint arranged to couple the needle to a portion of the spring assembly.

8. The apparatus of claim 1, wherein the first position indicates the movement of the needle corresponding to the depth of tissue penetration.

9. An apparatus, comprising:
   an intravascular delivery device, comprising:
      a needle to contact and penetrate tissue; and
      a device, comprising (1) a first conductive component coupled to the needle; and (2) a second conductive component disposed at a predetermined distance from the first conductive component prior to movement of one of the first and the second conductive components, the second conductive component being configured to indicate electronically when the second conductive component is in a first position, wherein one of the first conductive component and the second conductive component is selected to move in response to movement of the needle penetrating the tissue and wherein a movement corresponds to a depth of tissue penetration, the depth of tissue penetration corresponding to a specific location within the tissue for delivery of a treatment agent.

10. The apparatus of claim 9, further comprising:
    a spring assembly coupled to the needle and the first conductive component, the spring assembly adapted to separate the first conductive component from the second conductive component.

11. The apparatus of claim 10, wherein the spring assembly includes a spring machined out of a proximal portion of the needle.

12. The apparatus of claim 11, further comprising:
    weld joints arranged to couple the spring to a proximal and a distal part of the needle.

13. The apparatus of claim 10, further comprising:
    a slip-fit joint arranged to couple the needle tip to the proximal portion of the needle assembly.

14. The apparatus of claim 10, further comprising a weld joint arranged to attach proximal end of the spring assembly to proximal portion of the needle.

15. The apparatus of claim 9, further comprising:
    an insulator disposed on the needle in a region between the first conductive component and the second conductive component, the region including an area where the first conductive component is adapted to move to prevent the second conductive component from contacting the needle.

16. The apparatus of claim 9, wherein the first position indicates the movement of the needle corresponding to the depth of tissue penetration.

* * * * *